United States Patent [19]

Duffett

[11] Patent Number: Plant 5,495

[45] Date of Patent: Jun. 18, 1985

[54] CHRYSANTHEMUM PLANT NAMED EXCEL

[75] Inventor: William E. Duffett, Salinas, Calif.

[73] Assignee: Yoder Brothers, Inc., Barberton, Ohio

[21] Appl. No.: 468,034

[22] Filed: Feb. 18, 1983

[51] Int. Cl.[3] ..... A01H 1/00

[52] U.S. Cl. ..... Plt./76

[58] Field of Search ..... Plt./76, 80

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Excel having flat capitulum form; decorative capitulum type; lavender ray floret color; diameter across face of capitulum ranging from 55 to 70 mm. at maturity; uniform eight week photoperiodic flowering response to short days; tall plant height when grown as a pinched, spray pot mum, and spreading branching pattern.

3 Drawing Figures

The present invention comprises a new and distinct cultivar of *Chrysanthemum morifolium,* Ramat., named Excel.

Excel is a product of a planned breeding program which had the objective of creating new chrysanthemum cultivars for spray pot mum programs having decorative capitulum type, lavender ray floret color, eight week flowering response and the ability to produce commercially acceptable quality in year round programs. Such traits in combination were not present or required improvement in previously available commercial cultivars.

Excel was originated from a cross made in a controlled breeding program in Salinas, Calif. in 1978. The female parent was Tempo, disclosed in U.S. Plant Pat. No. 4,505, and originated by the present inventor from a hybridization of (Royal Purple×Mandalay)×(Snowpink×Pamplemousse). The male parent of Excel was an unnamed pink decorative seedling originated from a cross between Festival (unpatented but commercially available) and an unnamed pink decorative seedling.

Excel was discovered and selected as one flowering plant within the progeny of the stated cross by William E. Duffett on June 16, 1980 in a controlled environment in Salinas, Calif.

The first act of asexual reproduction of Excel was accomplished when vegetative cuttings were taken from the initial selection in November, 1980 in a controlled environment in Salinas, Calif. by a technician working under formulations established and supervised by William E. Duffett. Horticultural examination of selected units initiated April 1981 has demonstrated that the combination of characteristics as herein disclosed for Excel are firmly fixed and are retained through successive generations of asexual reproduction.

Excel has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

The following traits have been repeatedly observed and are determined to be basic characteristics of Excel which in combination distinguish this chrysanthemum as a new and distinct cultivar:

(1) Flat capitulum form;

(2) Decorative capitulum type;

(3) Lavender ray floret color;

(4) Diameter across face of capitulum ranging from 55 to 70 mm. at maturity;

(5) Uniform eight week photoperiodic flowering response to short days;

(6) Tall plant height requiring 1–2 long day weeks prior to pinch and short days, and 1–2 applications of 2500 ppm B-9 after the beginning of short days to attain a flowered plant height of 25 to 35 cm., and (7) A spreading branching pattern.

The accompanying photographic drawings depict typical foliage and inflorescence characteristics of Excel. Sheet 1 is a color photograph of a plant of Excel grown as a pinched spray pot mum, with colors being as accurate as possible with renditions of this type. Sheet 2 is a black and white photograph of three views of the inflorescence of Excel. Sheet 3 shows the leaves of Excel in three stages of development (mature, intermediate and immature).

Of the many commercial cultivars known to the present inventor, the most similar in comparison to Excel is Always Pink (commercially available). Reference is made to attached Chart A which compares certain characteristics of Excel to those same characteristics of Always Pink.

Excel is similar to Always Pink in capitulum form and type, diameter across face of capitulum and flowering response period.

Excel differs from Always Pink by having a deeper, more intense color, a greater resistance to color fading, a more spreading habit of growth and a taller plant height.

In the following description, color references are made to The Royal Horticultural Society Colour Chart. The color values were determined between 11:30 A.M. and 12:00 P.M. on Dec. 9, 1982 under 150 foot-candle light intensity at Salinas, Calif.

CLASSIFICATION:

*Botanical.*—*Chrysanthemum morifolium,* Ramat., cv Excel.

*Commercial.*—Spray decorative pot mum.

INFLORESCENCE

A. Capitulum:

*Form.*—Flat.

*Type.*—Decorative.

*Diameter across face.*—55 to 70 mm.

B. Corolla of ray florets:

*Color (general tonality from a distance of three meters).*—Lavender.

*Color (abaxial).*—Winter: 78B, 78C. Summer: 63C.

*Color (adaxial).*—Winter: 78D, Summer: 63D.

*Shape.*—Narrow, oblong, rounded tip.

C. Corolla of disc florets:

*Color (mature).*—154B.

*Color (immature).*—149C.

D. Reproductive organs:

*Androecium.*—Present disc florets only; very few; scant pollen.

*Gynoecium.*—Present both ray and disc florets.

PLANT

A. General appearance:

*Height.*—Tall; 25 to 35 cm. given 2 long day weeks before pinch and lights out, and 1–2 applications of 2500 ppm B-9 SP after lights out.

*Branching pattern.*—Spreading and prolific.

B. Foliage:

*Color (abaxial).*—137A.

*Color (adaxial).*—147B.

*Shape.*—Shallow lobes. Moderately serrate.

CHART A

COMPARISON OF EXCEL AND ALWAYS PINK

| CULTIVAR | RAY FLORET COLOR | CAPITULUM FORM AND TYPE | BRANCHING PATTERN |
|---|---|---|---|
| EXCEL | LAVENDER | FLAT DECORATIVE | SPREADING |
| ALWAYS PINK | DARK PINK | FLAT DECORATIVE | UPRIGHT |

| CULTIVAR | DIAMETER ACROSS FACE OF CAPITULUM | PLANT HEIGHT | FLOWERING RESPONSE PERIOD |
|---|---|---|---|
| EXCEL | 55 to 70 mm. | TALL 25 to 35 cm. | EIGHT WEEKS |
| ALWAYS PINK | 55 to 70 mm. | SHORT 20 to 30 cm. | EIGHT WEEKS |

COMPARISONS MADE OF PLANTS GROWN AS PINCHED, SPRAY POT MUMS IN SALINAS, CALIFORNIA AND LEAMINGTON, CANADA

I claim:

1. A new and distinct cultivar of *Chrysanthemum morifolium,* Ramat., named Excel, as described and illustrated, and particularly characterized as to uniqueness by the combined characteristics of flat capitulum form; decorative capitulum type; lavender ray floret color; diameter across face of capitulum ranging from 55 to 70 mm. at maturity; uniform eight week flowering response; tall plant height, and spreading branching pattern.

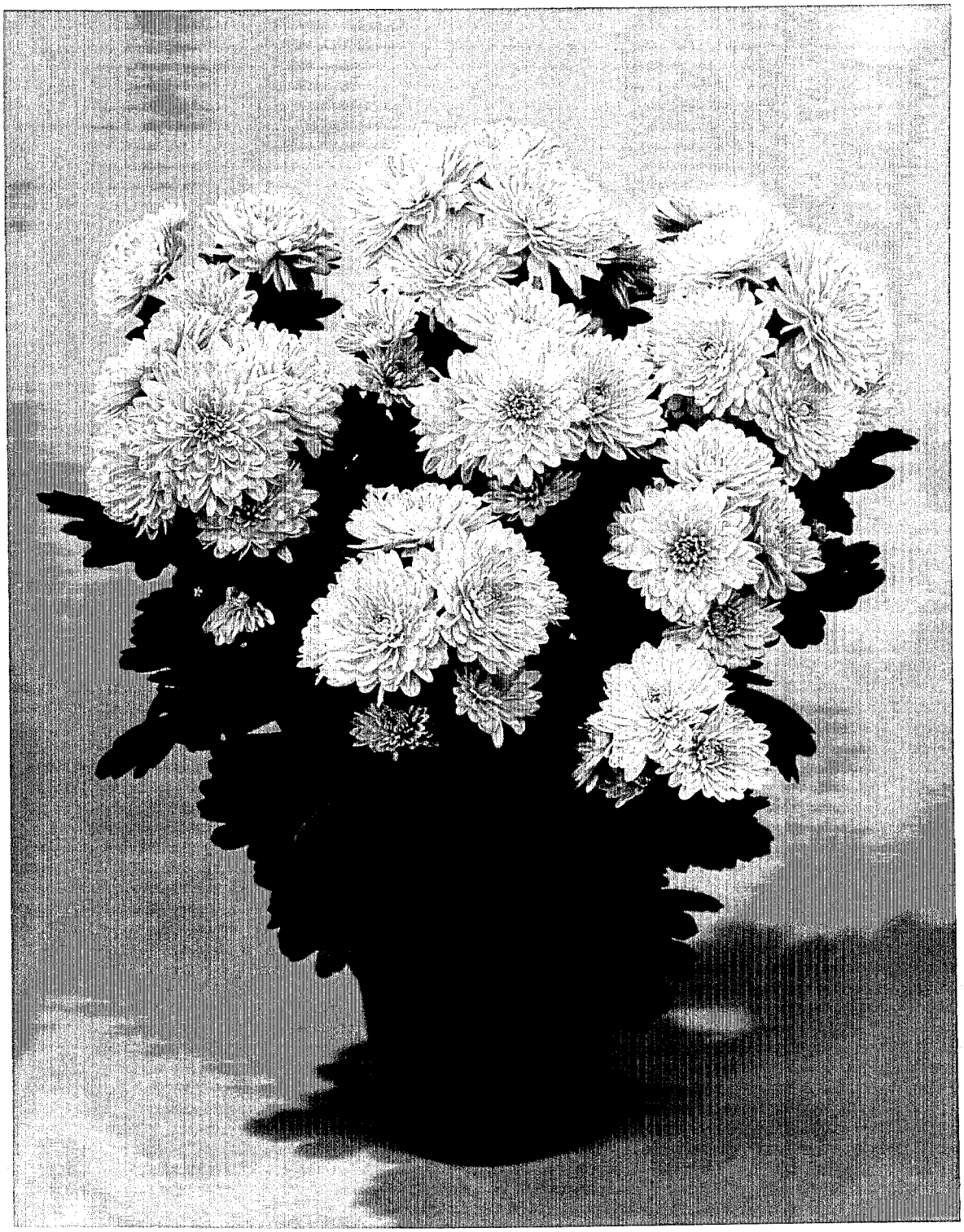

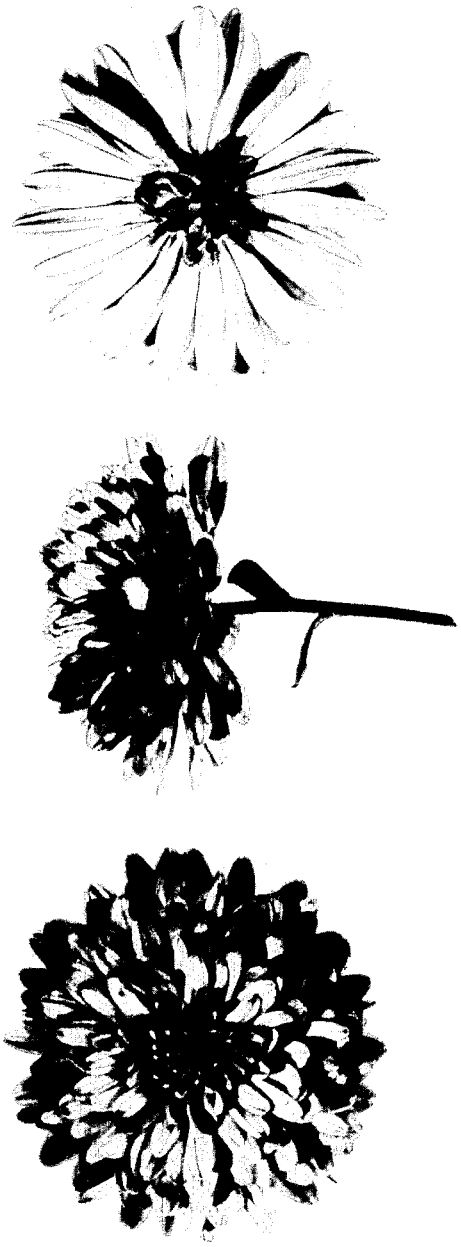

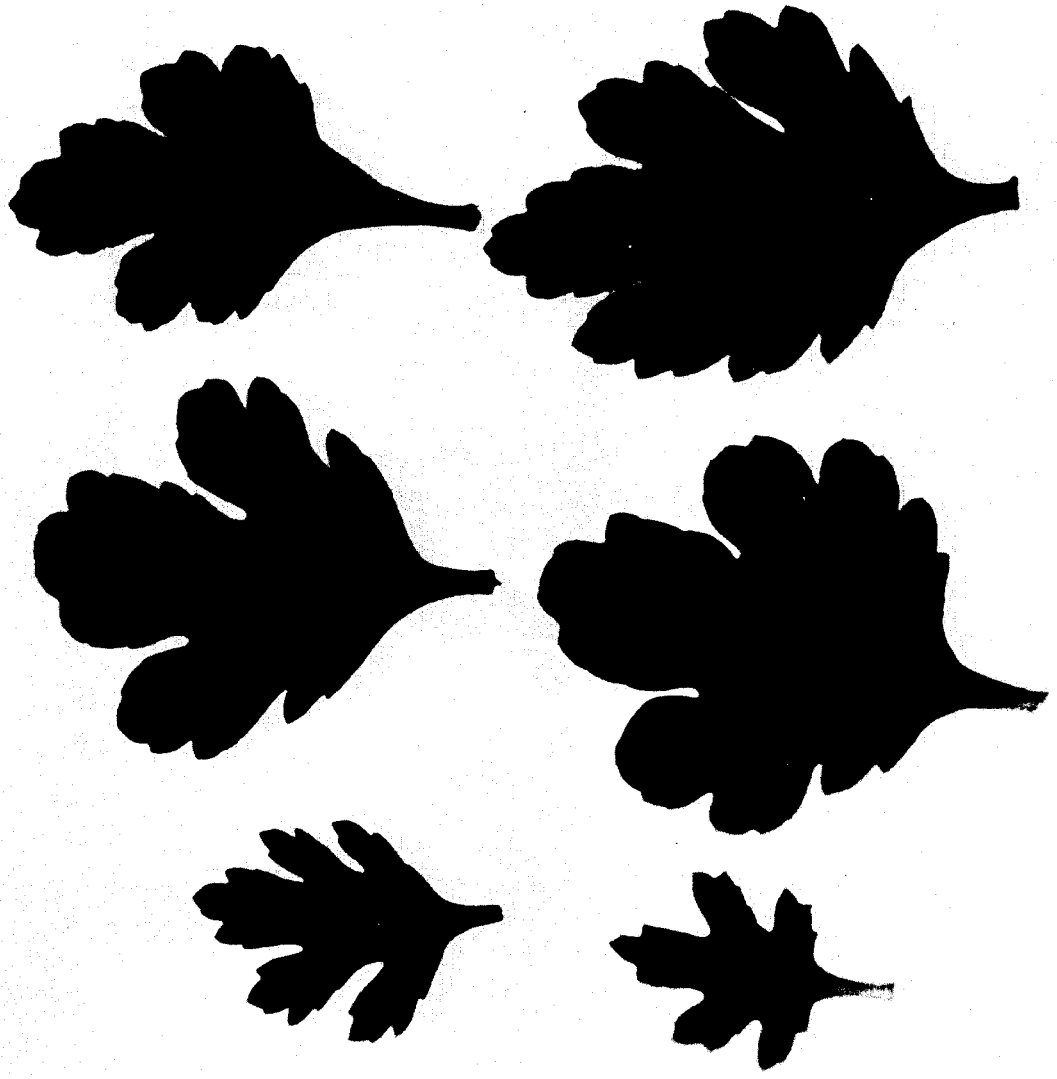

* * * * *